United States Patent
Walter et al.

(10) Patent No.: US 11,915,800 B2
(45) Date of Patent: Feb. 27, 2024

(54) PATIENT RECRUITMENT SYSTEM AND PATIENT RECRUITMENT METHOD

(71) Applicant: CLINERION LTD, Basel (CH)

(72) Inventors: Andreas Walter, Baden-Baden (DE); Ulf Claesson, Wettswil (CH); Dominik Aronsky, Rueschlikon (CH); Bernhard Bodenmann, Binningen (CH)

(73) Assignee: CLINERION LTD, Basel (CH)

( * ) Notice: Subject to any disclaimer, the term of this patent is extended or adjusted under 35 U.S.C. 154(b) by 542 days.

(21) Appl. No.: 15/307,092

(22) PCT Filed: Apr. 29, 2015

(86) PCT No.: PCT/EP2015/059415
§ 371 (c)(1),
(2) Date: Oct. 27, 2016

(87) PCT Pub. No.: WO2015/166005
PCT Pub. Date: Nov. 5, 2015

(65) Prior Publication Data
US 2017/0053069 A1 Feb. 23, 2017

(30) Foreign Application Priority Data
Apr. 30, 2014 (DE) .................... 10 2014 106 112.8

(51) Int. Cl.
*G16H 10/20* (2018.01)
*G16H 10/60* (2018.01)
*G06F 16/9535* (2019.01)

(52) U.S. Cl.
CPC ............. *G16H 10/20* (2018.01); *G16H 10/60* (2018.01); *G06F 16/9535* (2019.01)

(58) Field of Classification Search
CPC ............... G06F 17/30867; G06F 19/00; G06F 16/9535; G06F 16/958; G06F 21/6254; G06H 10/60; G06H 10/20
See application file for complete search history.

(56) References Cited

U.S. PATENT DOCUMENTS 7,904,313 B2   3/2011  Knight
9,471,637 B2 * 10/2016  New .................... G06F 21/6254
(Continued)

FOREIGN PATENT DOCUMENTS

AT         12796 U1      11/2012
CA       2337665 A1       8/2002
(Continued)

OTHER PUBLICATIONS

Neubauer, Thomas; Heurix, Johannes; "A Methodology For The Pseudonymization Of Medical Data," International Journal of Medical Informatics, vol. 80 No. 3, Mar. 2011, pp. 190-204, ISSN 1386-5056 (Year: 2011).*

(Continued)

*Primary Examiner* — Rachel L. Porter
(74) *Attorney, Agent, or Firm* — MH2 TECHNOLOGY LAW GROUP, LLP

(57) ABSTRACT

The invention is based on a patient recruitment system (10) having at least one patient recruitment server (16), which comprises at least one search routine (70) that is provided to search for patient data records (32) on the basis of recruitment characteristics (66).
It is proposed that the patient recruitment server (16) comprises a notification routine (82) which is provided to send a recruitment notification (76) regarding at least one patient data record (32) found on the basis of the recruitment characteristics (66).

9 Claims, 5 Drawing Sheets

(56) References Cited

U.S. PATENT DOCUMENTS

Figure 1:
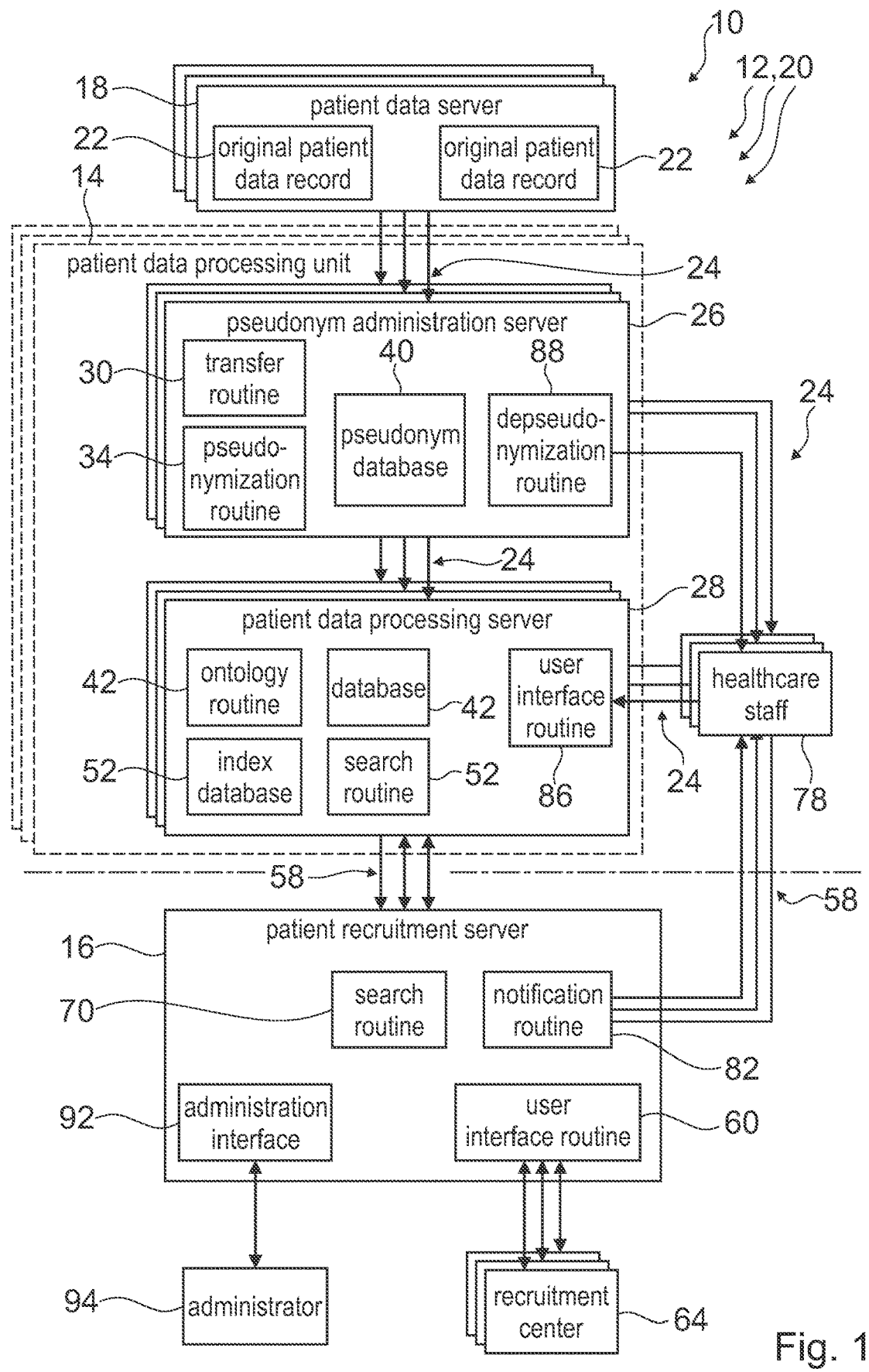

| | | | |
|---|---|---|---|
| 2005/0236474 A1 | 10/2005 | Onuma et al. | |
| 2005/0256380 A1* | 11/2005 | Nourie | G16H 10/60 600/300 |
| 2005/0267782 A1* | 12/2005 | Zahlmann | G16H 10/20 705/3 |
| 2007/0294110 A1* | 12/2007 | Settimi | G16H 10/60 705/3 |
| 2011/0112970 A1* | 5/2011 | Yu | G06Q 40/00 705/51 |
| 2011/0258000 A1* | 10/2011 | Green, III | G16H 10/20 705/3 |
| 2012/0191749 A1 | 7/2012 | New et al. | |
| 2013/0191161 A1 | 7/2013 | Churchwell et al. | |
| 2013/0304542 A1 | 11/2013 | Powell | |
| 2014/0289001 A1* | 9/2014 | Shelton | G06F 21/6254 705/7.29 |
| 2014/0304197 A1* | 10/2014 | Jaiswal | G06F 21/6209 706/12 |
| 2014/0343925 A1* | 11/2014 | Mankovich | G06F 40/30 704/9 |
| 2014/0372149 A1 | 12/2014 | Friese et al. | |

FOREIGN PATENT DOCUMENTS

| | | | |
|---|---|---|---|
| DE | 102007026802 A1 | 12/2007 | |
| WO | 2005098736 A2 | 10/2005 | |
| WO | 2013/124014 A1 | 8/2013 | |
| WO | 2013188838 A2 | 12/2013 | |
| WO | WO-2014088593 A1 * | 6/2014 | G06F 19/322 |

OTHER PUBLICATIONS

German Search Report dated Nov. 20, 2014, German Application No. DE 10 2014 106 112.8, filed Apr. 30, 2014, pp. 1-13 (including partial English Translation).

Author Unknown, European Office Action dated Sep. 1, 2020, EP Application No. 15722679.6, (English translation only), pp. 1-5.

Thomas Daub, Response to 1st Office Action filed May 17, 2019, EP Application No. 15722679.6 (English translation only), pp. 1-10.

Author Unknown, European Office Action dated Feb. 20, 2019, EP Application No. 15722679.6, (English translation only), pp. 1-4.

Dehns Ltd., Opposition dated Apr. 28, 2022, EP Patent No. 3138030, 62 pages.

Claerhout et al., Privacy protection for clinical and genomic data The use of privacy-enhancing techniques in medicine, International Journal of Medical Informatics, 2005, 74, pp. 257-265.

Schmid, Reply to the Opposition Division's Preliminary Opinion dated Feb. 27, 2023, EP Application No. 15722679.6, 103 pages.

Delaney et al., Envisioning a Learning Health Care System: The Electronic Primary Care Research Network, A Case Study, Annals of Family Medicine, vol. 10, No. 1, Jan. / Feb. 2012, 6 pages.

McMurry et al., A Self-scaling, Distributed Information Architecture for Public Health, Research, and Clinical Care, Journal of the American Medical Informatics Association, vol. 14, No. 4, Jul. / Aug. 2007, pp. 527-533.

McMurry et al., SHRINE: Enabling Nationally Scalable Multi-Site Disease Studies, PLOS One, vol. 8, Issue 3, Mar. 2013, 11 pages.

* cited by examiner

PATIENT RECRUITMENT SYSTEM AND PATIENT RECRUITMENT METHOD

CROSS REFERENCE TO RELATED APPLICATIONS

This application is a national-stage entry of PCT/EP2015/059415, filed Apr. 29, 2015, which claims priority to German Patent Application No. DE 102014106112.8, filed Apr. 30, 2014, the contents of all of which are hereby incorporated by reference in their entirety.

STATE OF THE ART

A patient recruitment system with at least one patient recruitment server having at least one search routine has already been proposed, the search routine being provided to search for patient data records on the basis of recruitment characteristics.

DISCLOSURE OF THE INVENTION

The invention relates to a patient recruitment system, in particular for recruiting patients in the areas of medicine and/or veterinary medicine, having at least one patient recruitment server which comprises at least one search routine provided to search for patient data records on the basis of recruitment characteristics.

It is proposed that the patient recruitment server comprises a notification routine which is provided to dispatch a recruitment notification regarding at least one patient data record found on the basis of the recruitment characteristics.

A "patient recruitment server" is to be understood, in particular, as a server, in particular centrally arranged server, and/or another controlling body, in particular centrally arranged controlling body, which is provided for patient recruitment in a plurality of healthcare institutions, in particular hospitals, and to this purpose, in at least one operating state, in particular on request from a patient data processing unit, transfers encoded search requests to patient data processing units. The patient recruitment server is preferably embodied as a dedicated server but could, as an alternative, also be embodied as a virtual server, as a plurality of distributedly located servers or as a server in a cloud. The patient recruitment server is preferentially situated outside the intranets of respective health information systems, e.g. respective hospital information systems, medical practice information systems, cancer registries or similar systems comprising patient data or patient-related data, of a healthcare institution, in particular of a hospital. The patient recruitment server is preferably provided for recruiting patients for a procedure deemed expedient by a person skilled in the art, advantageously for clinical surveys and/or for an organ transplantation. Preferentially patient data processing units of the patient recruitment system and the patient recruitment server communicate by means of a server-to-server communication deemed expedient by a person skilled in the art. The patient data processing units preferably communicate with the patient recruitment server in an encoded manner, e.g. via a VPN tunnel. A "healthcare information system" is to be understood, in particular, as a data processing system of a healthcare institution, in particular of a hospital, which data processing system is provided to administrate patient data records, in particular electronic patient records, for a use in the and/or by the healthcare institution. The healthcare information system preferably comprises a client-server structure. In particular, a patient data server of the healthcare information system is provided to dispatch the patient data records to one of the patient data processing units, in particular via an intranet of the healthcare information system. A "search routine" is to be understood, in particular, as a routine which is provided to find such patient data records that contain at least one given recruitment characteristic. The search routine is preferably provided to transmit a recruitment information to at least one unit, in particular the patient data processing units and/or an index database of at least one of the patient data processing units, and to receive a search result, in particular details regarding a frequency of a relevant search request from the patient recruitment server. Advantageously a search result transmitted by the patient data processing units contains, at least in case of extensive requests, in particular extensive requests having a plurality of recruitment characteristics, a respective indication of relevant search criteria and/or recruitment characteristics for each suitable patient and/or patient data record. In particular, the patient recruitment server is provided to generate, on the basis of the search results, an aggregated result and/or an aggregated report, in particular regarding a plurality of patient data records, search runs, queries, recruitment characteristics and sites, and to output these/this in particular via a user interface routine. The term "provided" is to mean, in particular, specifically programmed, designed and/or equipped. By an object being "provided for a specific function" is in particular to be understood that the object fulfills and/or carries out said specific function in at least one application state and/or operating state. By a "patient data record" in particular data are to be understood comprising information on a patient who has at least been examined in a healthcare institution, in particular in a hospital. The patient data records received by the patient data processing units preferably comprise at least portions of electronic patient records of the healthcare information system. A "recruitment characteristic" is intended to mean, in particular, a requirement which is fulfilled by a partial quantity of the patient data records. The recruitment characteristic can include patient data records into the partial quantity or exclude patient data records from the partial quantity. The recruitment characteristic is implemented as a characteristic deemed expedient by a person skilled in the art, e.g. as a minimum age, as a maximum age, as a diagnosis, as a laboratory result, as a sensor value, as a medication and/or as a weight. In particular, the term "search on the basis of recruitment characteristics" is to mean that the search routine is provided to determine the partial quantity of the patient data records which complies with the criteria of the recruitment characteristics. The search routine preferably identifies at least pseudonym information of the patient data records which complies with the criteria of the recruitment characteristics.

A "notification routine" is intended to mean, in particular, a routine which is provided to dispatch an electronic and/or non-electronic message, e.g. a list, an email, a text message and/or a pager message, and/or equivalently to initiate dispatch via a third site. As an alternative or additionally, the notification routine could dispatch a system-internal notification of the patient recruitment system to the healthcare staff. A "patient data record found by means of the recruitment characteristics" is in particular to be understood as a portion of the searched patient data records which meets the requirements defined by the recruitment characteristics. In particular, a "recruitment notification" is to be understood as a notification that at least lets the healthcare staff know that a patient is to be recruited. The recruitment notification preferentially comprises the recruitment information of at least one patient data record. As an alternative, the recruitment notification could comprise a pseudonymized patient data record.

The implementation of the patient recruitment system according to the invention allows advantageously short-term recruitment at particularly low staff input.

It is further proposed that the search routine is provided to repeatedly search the patient data records on the basis of the recruitment characteristics, thus advantageously allowing new and modified patient data records to be used for recruitment. As an alternative or additionally, the search routine could search solely new and modified patient data records.

Moreover, it is proposed that the notification routine is provided to automatically dispatch the recruitment notification regarding patient data records that have been newly found on the basis of the recruitment characteristics, as a result of which the healthcare staff is advantageously quickly informed of new patients who are suitable for recruitment. In particular, "patient data records that have been newly found" are to be understood as patient data records found in a search run which were not found in a previous search run. In particular, the newly found patient data records may have been added to the searched patient data records recently in between search runs, or may be found for the first time due to a modification of the recruitment information and/or of the recruitment characteristics. "Automatically" is in particular to mean that the notification routine dispatches the recruitment notification independently from the recruitment center. As an alternative, the recruitment notification could be dispatched after clearance by the recruitment center.

It is also proposed that the searched patient data records are implemented as pseudonymized patient data records, as a result of which the patient data may be used for a recruitment, in particular for a clinical survey, in an optimum way without breach of data protection principles. A "pseudonymized patient data record" is to mean a patient data record comprising no information by means of which a patient can be identified in a direct and/or simple manner.

Furthermore, it is proposed that the patient recruitment system has a plurality of distributedly located, in particular institution-internal and/or healthcare institution-internal, patient data processing units which, in at least one operating state, respectively receive patient data records from at least one healthcare information system, in particular a hospital information system, thus allowing for advantageous processing of the patient data records inside the intranets of the healthcare institutions. A "patient data processing unit" is in particular intended to mean a unit which, in at least one operating state, receives and processes patient data records. The patient data processing unit preferably comprises at least one server, particularly preferably a plurality of servers. In particular, the patient data processing unit is connected, via a communication connection, to a healthcare information system of a healthcare institution, in particular of a hospital. The patient data processing unit is preferably protected against an unauthorized access in particular by means of an IT infrastructure of the healthcare institution, in particular the hospital, and/or advantageously by means of measures integrated in the patient data processing unit. There are preferentially organizational and/or preferably technical provisions installed which ensure that the pseudonymized patient data cannot leave the healthcare institution either. Advantageously each of the patient data processing units is arranged in a local network and/or an intranet, in particular of an IT department, of an institution and/or of a healthcare institution, in particular a hospital. In particular, patient data and/or patient data records do not leave the local network nor the intranet, as a result of which in particular data protection guidelines, e.g. a control of the patient data and/or patient data records, can be fulfilled. This in particular allows ensuring that the patient recruitment system is only provided with aggregated data, which may in particular be used for a presentation of search results. Preferably each of the patient data processing units is integrated in an intranet of different healthcare institutions.

In a further implementation it is proposed that each of the patient data processing units respectively comprises at least one depseudonymization routine provided to determine at least one patient identification information corresponding to a pseudonym information of the pseudonymized patient data records, thus allowing recruitment under especially effective data protection conditions. By a "depseudonymization routine" in particular a routine is to be understood which is provided to find and in particular output a corresponding patient identification information for a pseudonym information. Preferentially solely the healthcare staff can access the patient identification information determined by the depseudonymization routine. In particular, the recruitment center cannot access the patient identification information determined by the depseudonymization routine. A "patient identification information" is to mean, in particular, an information allowing to deduce an identity of a patient, e.g. a first name, a surname and a birth date. As an alternative or additionally, the patient identification information could comprise an identification information that has been allocated to the patient data record by the healthcare information system, and at least the name of the patient could be identified via the healthcare information system. By a "pseudonym information" in particular an information is to be understood which bijectively identifies a patient data record without allowing conclusions to a patient's identity, e.g. an identification number.

It is moreover proposed that each of the patient data processing units comprises at least one pseudonym administration server which, in at least one operating state, stores the pseudonym information and the corresponding patient identification information, thus allowing particularly efficient protection of the patient identification information. A "pseudonym administration server" is to be understood, in particular, as a server which is provided to allow an allocation of a pseudonym information and a patient identification information. Preferentially a respective pseudonym administration server is allocated to each patient data processing server.

It is also proposed that the recruitment notification comprises at least the pseudonym information and/or the patient identification information, as a result of which the patient who is to be recruited is advantageously identifiable.

Furthermore, it is proposed that the patient data processing units have at least one respective pseudonymization routine, the pseudonymization routines being provided to pseudonymize patient data records received from healthcare information systems, as a result of which only such data leave a control of the healthcare institution in which allocation to a patient is at least substantially made difficult. By a "pseudonymization routine" in particular a routine is to be understood which is provided to remove at least information allowing direct conclusion to a patient's identity, e.g. names, addresses, birth dates and/or insurance numbers, from the patient data record. Preferably the pseudonymization routine removes further data deemed expedient by the person skilled in the art, namely data that allow indirect back-referencing from the patient data record to the patient's identity and/or are not necessary for patient recruitment. The pseudonymization routine preferably adds a bijective pseudonym information to the patient data record. In particular, the pseudonymization routine can copy and/or modify the information of the received patient data records for generating the pseudonymized patient data records.

It is also proposed that the patient data processing units are provided to output at least the patient identification information to a healthcare staff, as a result of which the patient belonging to a patient data record may be identified by the healthcare staff under advantageous protection against unauthorized access. Preferably the pseudonym administration servers, particularly preferentially the depseudonymization routines of the pseudonym administration servers, are provided to output at least the patient identification information to a healthcare staff.

Furthermore, it is proposed that the patient data processing units have at least one respective user interface routine, the user interface routines being provided to at least partially output at least one of the patient data records to the healthcare staff, thus allowing information advantageous for recruitment to be made available to the healthcare staff in a simple and comfortable manner. The user interface routines preferably output the at least one patient data record depending on the patient identification information and/or on the pseudonym information. The user interface routines preferentially output at least one of the pseudonymized patient data records and/or at least one of the original patient data records. In particular, the term "respective" is to mean, in this context, that the patient data processing units comprise user interface routines which are implemented separate from each other. Preferably the respective user interface routines are only accessible from an intranet of the healthcare information system and/or only after an authentification to the healthcare information system. In particular, the user interface routines each have their own respective authentification routine by means of which the authorized healthcare staff can be authentified. A "user interface routine" is to be understood, in particular, as a routine which is provided to process data for presentation. The user interface routine is implemented as a routine deemed expedient by the person skilled in the art, preferably as an http server. Preferentially the user interface routine dispatches data to a program designed for presentation of the data. The user interface routine is in particular provided to output the data only after an authentification, in particular a user authentification, has been successful. By a "healthcare staff" in particular persons are to be understood who are responsible for care and/or treatment of the patients in a healthcare institution, in particular in a hospital.

It is moreover proposed that the patient data processing units and in particular the user interface units of the patient data processing units are provided to collect at least one patient status information from the healthcare staff, thus allowing a result of the recruitment to be determined in a prompt and simple way. In particular, a "patient status information" is to be understood as an information that describes a status of a patient's recruitment procedure carried out by the healthcare staff. The patient status information preferentially shows status deemed expedient by the person skilled in the art, particularly preferably at least three status, namely advantageously at least the status "intended for recruitment", "not suitable" and "recruited". The patient status information could also show, for example, the status "further verification required" and "recruitment interview not yet done/possible".

In a further implementation of the invention it is proposed that the pseudonym administration servers, in at least one operating state, dispatch the pseudonymized patient data records, and that the patient data processing servers of the patient data processing units, in at least one operating state, receive the pseudonymized patient data records from the pseudonym administration servers, as a result of which a technical and spatial separation of the pseudonym administration server and the patient data processing server can be achieved, thus allowing an advantageously high level of data safety. The pseudonym administration server and the patient data processing servers preferably communicate solely via the intranet of the respective healthcare information system, in particular in an encoded fashion, e.g. via a VPN tunnel. The pseudonym administration servers and/or the patient data processing servers are preferably embodied as dedicated servers but could also, as an alternative, be embodied as virtual servers or as servers in a cloud, in particular in a cloud of the healthcare information system. In particular, the pseudonym administration server is embodied separate from the patient data processing server, and is connected to the patient data processing server by way of a communication path, in particular by way of the intranet of the healthcare information system. As an alternative, the pseudonym administration server could be integrated in the patient data processing server. Preferably there is a respective pseudonym administration server allocated to each patient data processing server.

It is further proposed that each of the patient data processing units comprises at least one ontology routine provided to standardize at least one ontology of the patient data records, as a result of which patient data records based on different ontologies can advantageously be searched on the basis of one ontology. Preferentially the patient data processing server comprises the ontology routine. As an alternative or in particular additionally, the patient recruitment server could comprise an ontology routine. In this context, an "ontology" is to be understood, in particular, as an in particular explicit formal specification of a conceptualization. The ontology can herein comprise in particular lists, thesauri, instance models and/or preferentially terminologies. An "ontology routine" is to mean, in particular, a routine which is provided to analyze a meaning of the characteristics of the patient data records and to convert these characteristics into characteristics complying with the standardized terminology. The ontology routine is implemented as an ontology routine deemed expedient by the person skilled in the art, which is in particular optimized to a medical terminology, e.g. a routine working according to UMLS (Unified Medical Language System) and/or according to the RxNorm. Preferably the ontology routine is provided to classify the characteristics of the patient data records at least according to a standardized target classification of the diseases and/or of the medical products or of similar ontologies. The target classification of the diseases is a target classification deemed expedient by the person skilled in the art, advantageously an "ICD" classification, e.g. ICD-10 or future ICD versions. The target classification of the medical products is a classification deemed expedient by the person skilled in the art, advantageously an "ATC" classification. The ontology routine in particular recognizes characteristics which have been classified according to a classification that differs from the target classification, e.g. classified according to ICD-9, SNOMED or NDC, and converts this classification into the target classification.

The ontology routine preferentially comprises a linguistics routine. Preferably the ontology routine comprises a terminologization routine. The linguistics routine is in particular provided to transfer free text into the standardized ontology, in particular into a standardized terminology, thus advantageously allowing characteristics of the standardized patient data records based on the free text to be searched. By a "linguistics routine" in particular a routine is to be understood which is provided to analyze a free text of the patient data records and to assign a meaning to respective characteristics of the free text. The linguistics routine is preferably implemented as a routine deemed expedient by the person skilled in the art, particularly advantageously as a "GATE" (General Architecture for Text Engineering) routine, which is in particular optimized to medical data. The term "free text" is to mean, in particular, a text the structure of which is based on the grammar rules of the language used. The terminologization routine is in particular provided to transfer a terminology of the patient data records of at least one of the healthcare information systems into a standardized terminology, thus allowing particularly effective searching of the patient data records. In particular, a "terminologization routine" is to mean a routine which is provided to analyze different terminologies of the patient data records, to assign a meaning to respective characteristics of the patient data records and to translate the characteristics into another, standardized terminology on the basis of their meanings.

It is further proposed that f the patient data processing units have at least one respective database provided to store the pseudonymized patient data records, thus allowing advantageously quick access to the patient data records. Preferentially the patient data processing servers of the patient data processing units each have a database. The term "database" is intended to mean, in particular, a means of the patient recruitment system, which means is provided for storing the patient data records. The database preferably comprises a plurality of tables. The database is embodied as a database deemed expedient by the person skilled in the art, e.g. as an SQL database.

It is also proposed that the patient recruitment server comprises at least one user interface routine which is provided to output at least one search result of the search routine to a recruitment center, thus allowing a selection of the recruitment characteristics to be advantageously examined. By a "search result", in particular information is to be understood which is provided to supply a user with a result of his search. The search result preferably comprises at least the pseudonym information and/or a patient identification information of the found patient data records. Preferably the search result comprises at least an information about a number of found patient data records. Advantageously the search result comprises the found patient data records. As an alternative or additionally, the search result could comprise links to the found patient data records. Particularly advantageously the search result comprises only data describing the found patient data records, as a result of which an especially high-level data protection may be achieved. A "recruitment center" is to mean, in particular, a user of the patient recruitment system, which user wishes to find patients, in particular for a clinical survey, by means of the patient recruitment system. The term "output" is to mean, in particular, that the recruitment center dispatches the search result to a device which presents the search result to the user.

In an advantageous implementation of the invention it is proposed that the user interface routine of the patient recruitment server is provided to collect a recruitment information from the recruitment center, thus allowing the recruitment center to search the patient data records for a variety of recruitment characteristics in an in particular structurally simple fashion. In particular, a "recruitment information" is to mean an information indicating that a patient is intended for recruitment. The recruitment center preferably selects such patients from the search result, whom the recruitment center wishes to recruit, in particular for a clinical survey. Preferentially the recruitment information comprises at least the pseudonym information of the patients selected on the basis of their patient data records. As an alternative, the recruitment information could tag the respective pseudonym information.

It is proposed, in a further implementation, that the patient data processing units are provided to search for the pseudonymized patient data records on the basis of recruitment characteristics linked by the recruitment information, thus allowing complex searches in particular in a structurally simple manner. Herein a linkage of the recruitment characteristics by way of the recruitment information may be effected using probability-based algorithms or similar algorithms of machine learning and/or using a fuzzy logic and/or preferably using logical operations, e.g. in particular AND, OR, NOT, SMALLER THAN, GREATER THAN, and/or using brackets, any of which creating a relationship between the recruitment characteristics.

It is further proposed that the user interface routine of the patient recruitment server is provided to output a number of found patient data records for respective ones of the linked recruitment characteristics, thus allowing to advantageously promptly discern which recruitment characteristics restrict the number of found patient data records to what degree. In particular, a "number of found patient data records" is to be understood as an information indicating how many patient data records, in this case for each of the recruitment characteristics respectively, have been found.

Furthermore, it is proposed that each of the patient data processing units has at least one index routine provided for indexing the patient data records, and/or processing for a search, in particular a semantic search, thus allowing especially quick searching in the patient data records. An "index routine" is to mean, in this context, a routine which is provided to generate, regarding the patient data records, an information that is optimized for searching The index routine is further provided for generating statistics, e.g. regarding a frequency of a recruitment characteristic, in particular of occurring diagnoses, laboratory data, treatments and/or procedures. Preferentially the index routine uses the meanings assigned to the characteristics of the patient data records by the terminologization routine.

It is also proposed that the user interface routine of the patient recruitment server is provided to output a number of found patient data records which originate from one of the healthcare information systems, as a result of which healthcare institutions, in particular hospitals, having a low number of suitable patients may advantageously be identified. The term "which originate from one of the healthcare information systems" is to mean that the user interface routine indicates how many patients come from each of the healthcare institutions operating the healthcare information systems.

In an advantageous implementation of the invention it is proposed that the patient data records comprise biomedical data, medical product data, laboratory data, personal data and/or sensor data, thus allowing particularly accurate selection of the patients. By "biomedical data" in particular data deemed expedient by the person skilled in the art are to be understood which refer to a diagnosis and/or an examination carried out by the healthcare staff, namely advantageously at least symptoms, diagnoses, procedures, treatments, therapy data and/or genetic data. In particular, "medical product data" are to mean data which describe the medical products with which a patient has been treated, is being treated and/or is to be treated, as in particular medical treatment apparatus, e.g. a treatment with a respiratory machine, and/or advantageously medication. "Laboratory data" are in particular to be understood as data found by a medical laboratory. "Personal data" are to be understood, in particular, as non-medical data describing the patient, e.g. a body size, an age, a sex, a weight and/or other data deemed expedient by the person skilled in the art. "Sensor data" are to mean, in particular, data taken from a patient by a sensor, e.g. an electrocardiogram, a blood pressure, a pulse rate, a blood sugar level, and/or further data deemed expedient by the person skilled in the art.

The invention furthermore relates to a patient recruitment method, in particular with a patient recruitment system according to the invention, wherein patient data records are searched on the basis of recruitment characteristics and a recruitment notification is dispatched when at least one patient data record has been found by means of the recruitment characteristics.

The patient recruitment system according to the invention and the patient recruitment method according to the invention are not intended to be restricted to the application and implementation described above. In particular, the patient recruitment system according to the invention and the patient recruitment method according to the invention may comprise, for achieving a functionality as herein described, a number of respective elements, components and units that differs from the respective numbers herein mentioned.

DRAWING

Further advantages may be gathered from the following description of the drawing. In the drawing an exemplary embodiment of the invention is shown. The drawing, the description and the claims comprise a plurality of features in combination. The person skilled in the art will purposefully also consider said features individually and then combine them in further expedient arrangements.

Figure 2:
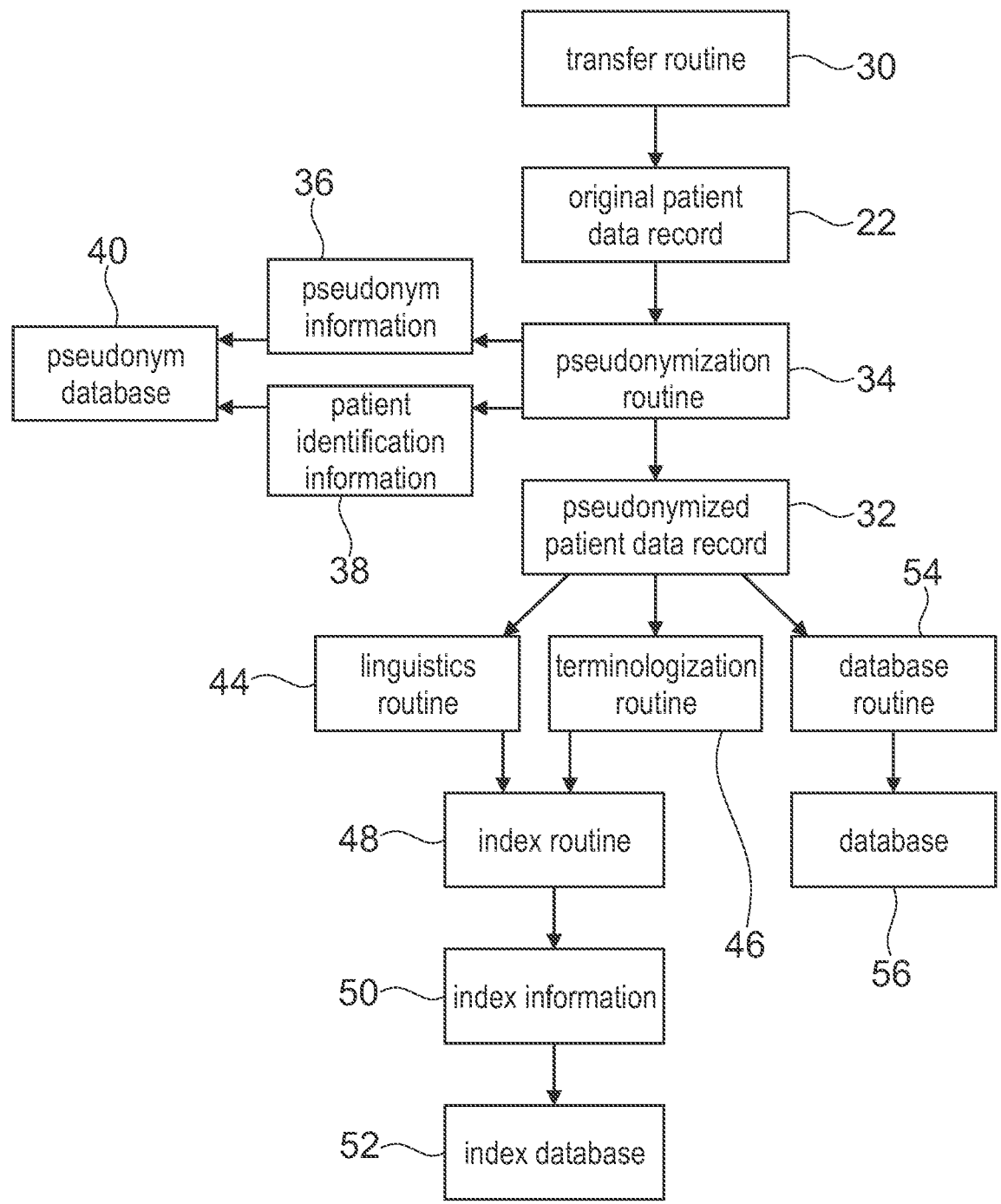
Figure 3:
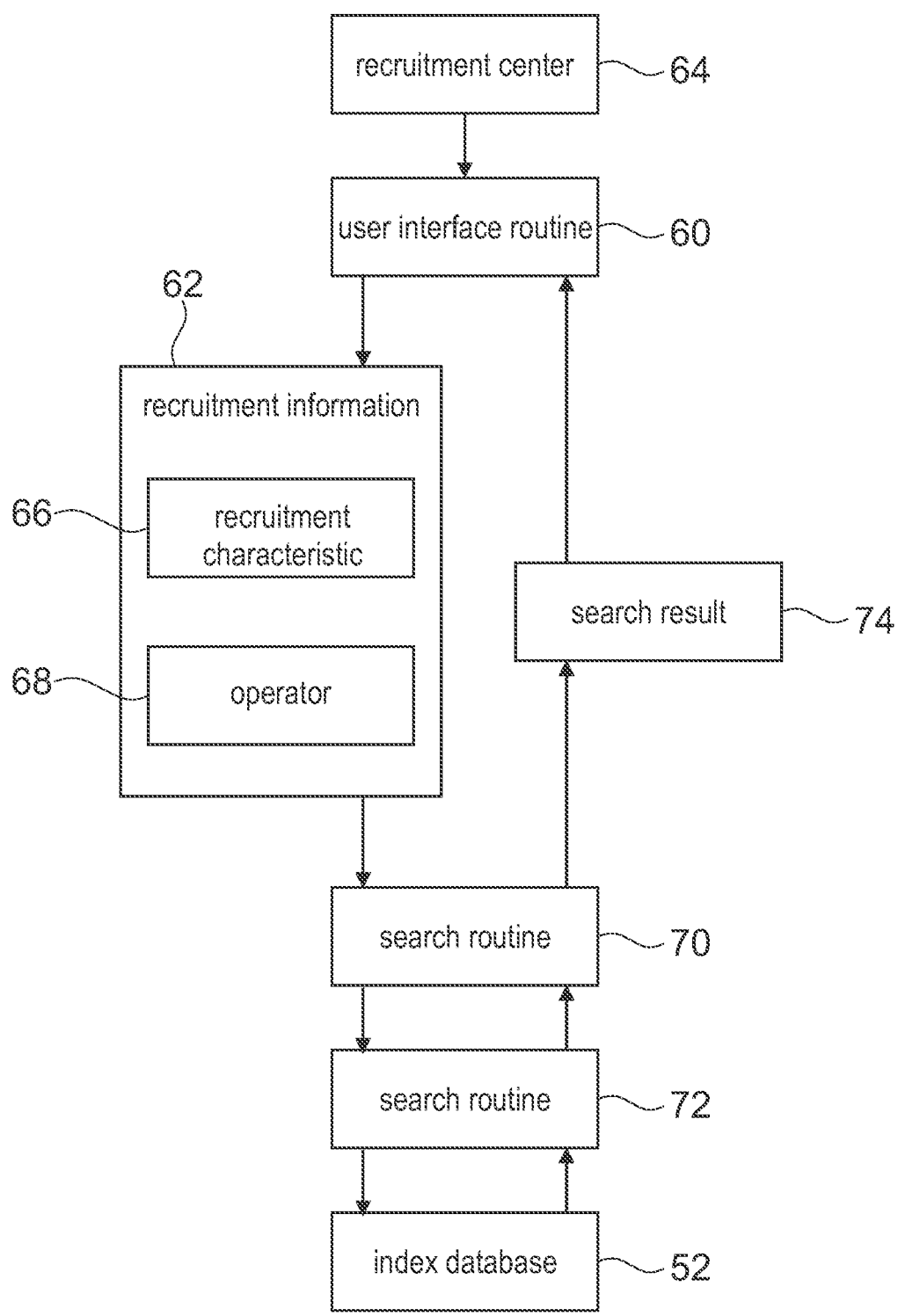
Figure 4:
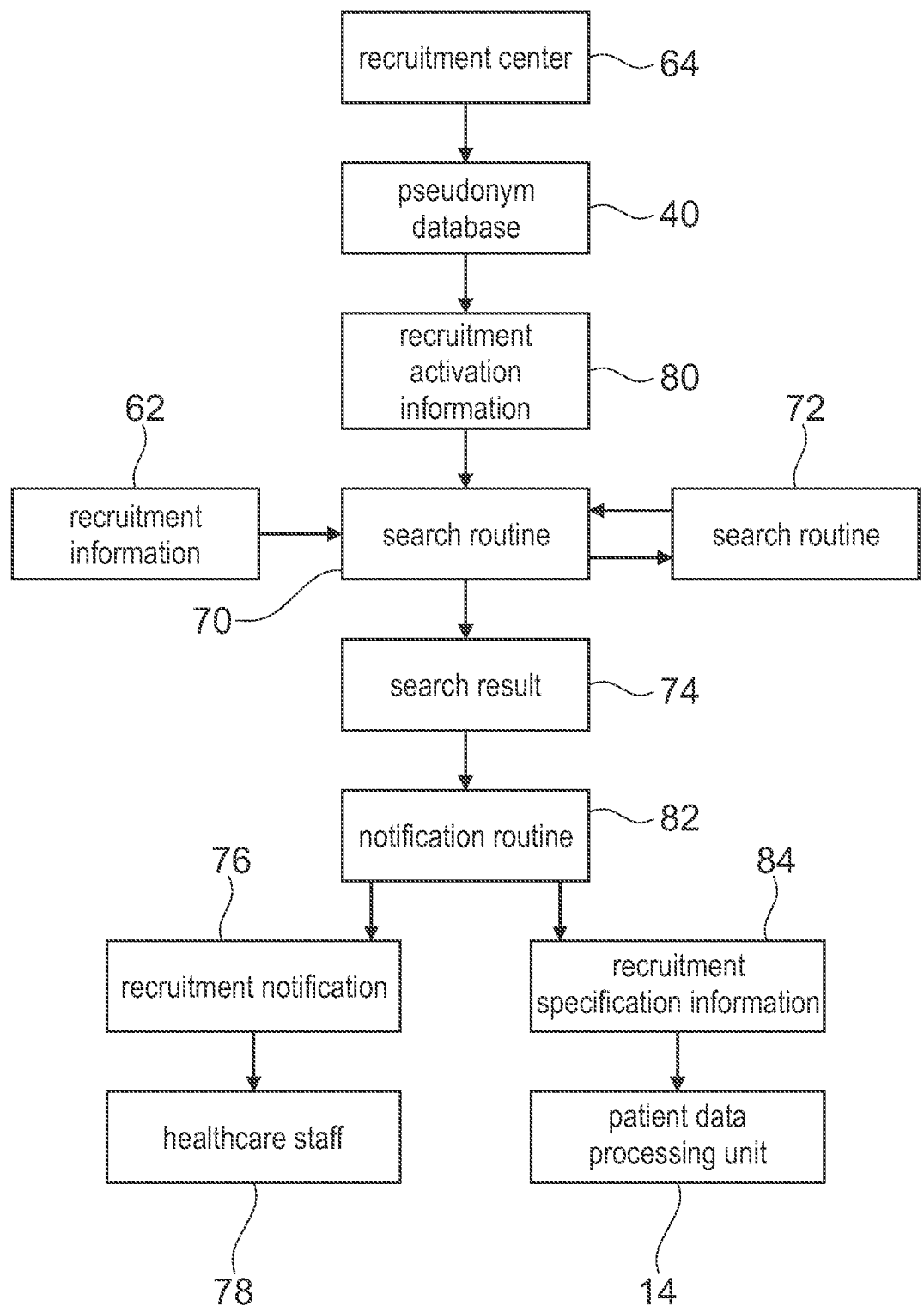
Figure 5:
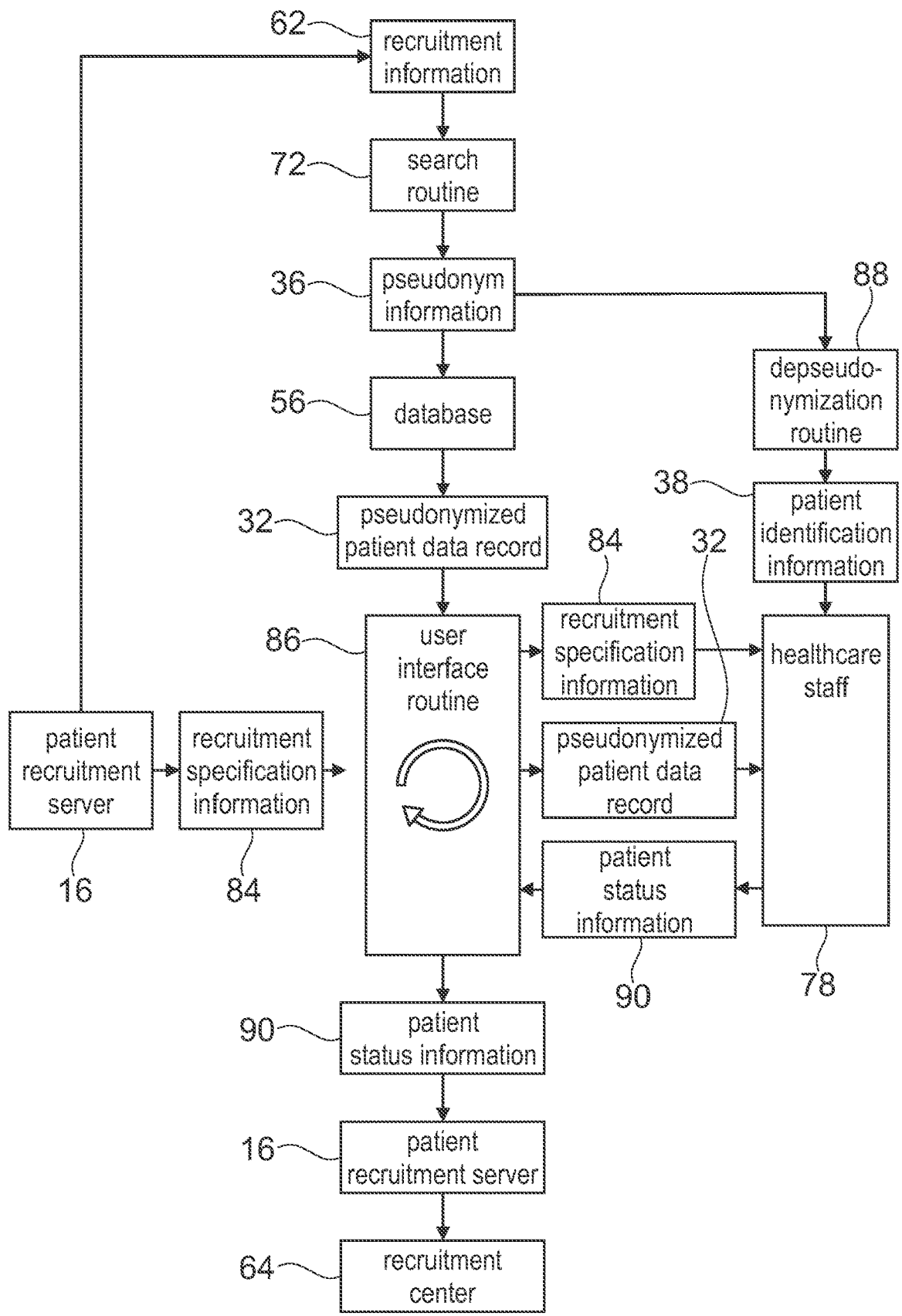

Shown in:

FIG. 1 is a patient recruitment system according to the invention for implementing a patient recruitment method according to the invention as a schematic image, FIG. 2 is a pseudonymization of patient data records via the patient recruitment method from FIG. 1, FIG. 3 is a search of patient data records via the patient recruitment method from FIG. 1, FIG. 4 is a notification of healthcare staff via the patient recruitment method from FIG. 1, and FIG. 5 is a recruitment information being collected by the healthcare staff via the patient recruitment method from FIG. 1.

DESCRIPTION OF THE EXEMPLARY EMBODIMENT

FIG. 1 shows a patient recruitment system 10 according to the invention, for implementing a patient recruitment method according to the invention, which method is described in detail in FIGS. 2 to 5. The patient recruitment system 10 comprises a plurality of patient data processing units 14, which are situated in different hospitals, and at least one patient recruitment server 16. In FIGS. 2 to 5 recruitment of patients by means of one of the patient processing units 14 is described. Recruitment by means of another one of the patient data processing units 14 is carried out in an equivalent manner.

The patient data processing units 14 receive, in at least one operating state, original patient data records 22 from patient data servers 18 of a healthcare information system 20 of the respective hospitals 12. The patient data servers 18 independently send newly generated and modified patient data records 22 to the patient data processing units 14. The patient data processing units 14 and the patient data servers 18 are connected to each other via an intranet 24 of the healthcare information system 20. The patient data records 22 are embodied as electronic health records. The patient data records 22 comprise biomedical data, medical product data, laboratory data, personal data and/or sensor data.

Each of the patient data processing units has a respective pseudonym administration server 26 and a patient data processing server 28. Transfer routines 30 of the pseudonym administration servers 26 receive, in at least one operating state, the patient data records 22 from the respective patient data servers 18. The pseudonym administration servers 26 are provided to pseudonymize the patient data records 22, thus generating pseudonymized patient data records 32. The pseudonym administration servers 26 forward the pseudonymized patient data records 32 to the patient data processing servers 28.

FIG. 2 shows part of the patient recruitment method, wherein the patient data records 22 of the patient data servers 18 are pseudonymized and a terminology of the patient data records 22 is standardized for indexing. The transfer routines 30 of the pseudonym administration servers 26 demand from the patient data servers 18, in predetermined intervals, at least modified or new ones of the original patient data records 22.

Pseudonymization routines 34 of the pseudonym administration servers 26 are respectively provided to respectively pseudonymize the received original patient data records 22 and to generate the pseudonymized patient data records 32. To this purpose, the pseudonymization routine 34 respectively searches the entire received original patient data record 22 for information by which to directly identify the patient whom the patient data record 22 belongs to. The pseudonymization routine 34 generates the pseudonymized patient data record 32 which does not contain the information mentioned above. The pseudonymization routine 34 comprises self-learning functions provided to remove the information which could directly identify the patient from free text that may be contained.

The pseudonymization routine 34 creates a pseudonym information 36 which bijectively identifies the pseudonymized patient data record 32, and then adds the pseudonym information 36 to the pseudonymized patient data record 32. The pseudonymization routine 34 determines a patient identification information 38 from information by which the patient whom the original patient data record 22 corresponds to is directly identifiable. The patient identification information 38 comprises at least a surname, a first name and advantageously a birthdate of the patient. Hence the patient is bijectively identifiable by means of the patient identification information 38.

The pseudonymization routine 34 stores the pseudonym information 36 and the patient identification information 38, which are assigned to each other, into a pseudonym database 40 of the respective pseudonym administration server 26. The pseudonym database 40 stores the pseudonym information 36 and the patient identification information 38, the one assigned to the other one. The pseudonym database 40 is specifically protected from unauthorized access.

The pseudonym administration server 26 sends the pseudonymized patient data record 32 to the patient data processing server 28. The pseudonym administration server 26 and the patient data processing server 28 communicate with each other solely via the intranet 24 of the healthcare information system 20. The patient data processing server 28 comprises an ontology routine 42.

The ontology routine 42 is provided to standardize at least one ontology of the pseudonymized patient data records 32 for indexing. As an alternative or additionally, the ontology routine 42 could generate a standardized patient data record. The ontology routine 42 comprises a linguistics routine 44 and a terminologization routine 46. The linguistics routine 44 is provided to analyze the meaning of characteristics of free text contained in the patient data records 32. To this purpose, the linguistics routine 44 comprises a "GATE" instance. From the free text, the linguistics routine 44 determines characteristics encoded according to a system, in particular ICD-10.

The terminologization routine 46 is provided to transfer a terminology of the characteristics of the patient data records 32 into a standardized terminology. The original patient data records 22 of the different healthcare information systems 20 may comprise characteristics which are encoded following different systems. The terminologization routine 46 comprises instances of transfer libraries deemed expedient by the person skilled in the art, which instances translate the differently encoded characteristics into identically encoded characteristics. In the present case, the terminologization routine 46 comprises at least a UMLS instance and an RxNorm instance.

The ontology routine 42 is further provided to find further characteristics, deemed expedient by the person skilled in the art, regarding the patient data records 32, e.g. information about the hospital 12 and/or quality information, in particular on terminologization. Moreover, self-learning functions could be applied for finding such characteristics.

The patient data processing server 28 comprises an index routine 48 which is provided for indexing the characteristics found by the ontology routine 42. The index routine 48 stores an index information 50 with the indexed characteristics in an index database 52 of the patient data processing server 28.

The patient data processing server 28 comprises a database routine 54 which is provided to store the pseudonymized patient data records 32. The database routine 54 stores the pseudonymized patient data records 32 in a database 56 of the patient data processing server 28. Each index information 50 contains a link to one of the pseudonymized patient data records 32 in the database 56.

The patient recruitment server 16 is located in a place different from the patient data processing units 14. In the present case, the patient data processing units 14 and the patient recruitment server 16 are connected to each other by means of an encoded connection via the Internet 58, namely via a VPN tunnel.

As shown in FIG. 3, the patient recruitment server 16 comprises a user interface routine 60, which is provided to supply users of the patient recruitment system 10 with information and to collect information from the users. In the present case, the user interface routine 60 comprises an HTML server. As an alternative, any other server type is conceivable. The user interface routine 60 could also be implemented as a server of a server-client structure, wherein programs of the patient recruitment system 10 installed and executed on the users' computers output the information to the users and collect information from the users.

The user interface routine 60 of the patient recruitment server 16 is provided to collect a recruitment information 62 from the user, who is embodied as a recruitment center 64. The recruitment center 64 consists, for example, of representatives of a pharmaceutic company wishing to carry out a clinical survey, of doctors who carry out the clinical survey and possibly of expert operatives of the patient recruitment system 10. For the clinical survey the recruitment center 64 is looking for suitable patients whom the recruitment center 64 wishes to recruit for carrying out the survey.

The recruitment information 62 comprises recruitment characteristics 66 and operators 68. The operators 68 logically link the recruitment characteristics 66 with each other. Recruitment characteristics 66 linked by the operators 68 may be grouped, for example, using brackets. Thus any type of logical term may be created from the recruitment characteristics 66. Entry of the recruitment information 62 is made in a text-based manner and is checked and implemented by means of a formula analyzer. As an alternative or additionally, an entry of the recruitment information 62 could also be made graphically.

The recruitment characteristics 66 may comprise biomedical data, medical product data, laboratory data, personal data and/or sensor data. The recruitment characteristics 66 are at least selectable from a quantity of encoded characteristics available with standardization of the patient data records 32. Moreover, value ranges may be determined by the recruitment characteristics 66 and the operators 68. The recruitment characteristics 66 may also comprise free search terms for which the free text of the patient data records 22 is searched.

The patient recruitment server 16 comprises a search routine 70 which is provided to search pseudonymized patient data records 32 by means of the index information 50 of the index database 52 of the patient data processing units 14 on the basis of the recruitment information 62. The search routine 70 of the patient recruitment server 16 dispatches at least the recruitment information 62 to search routines 72 of the patient data processing units 14. The search routines 72 of the patient data processing units 14 search the index databases 52 of the patient data processing units 14 on the basis of the recruitment information 62. The patient data processing unit 14 which the recruitment information 62 is sent to as well as the patient data processing unit 14 which carries out a search by means of the recruitment information 62 is respectively adjustable. The search routine 72 generates a search result 74 and dispatches the search result 74 to the patient recruitment server 16.

The search result 74 comprises at least an information about a number of found patient data records 32. The search result 74 also comprises a number of found patient data records 32 itemized for each of the recruitment characteristics 66 and in particular for grouped recruitment characteristics 66. The search result 74 moreover comprises a number of found patient data records 32 itemized for each of the hospitals 12. Furthermore, the search result 74 could comprise further information deemed expedient by the person skilled in the art as regards the found patient data records 32 and/or at least portions of the found patient data records 32. The search result 74 further comprises the pseudonym information 36 of the found patient data records 32. In particular, the search result 74 comprises no information suitable for directly identifying a patient whom one of the found patient data records 32 is allocated to.

The user interface routine 60 is provided to output the search result 74 of the search routine 70 to the recruitment center 64. Herein the user interface routine 60 outputs the number of found patient data records 32 for respective ones of the logically linked recruitment characteristics 66 and for a number of found patient data records 32 which originate from one of the healthcare information systems 20.

As shown in FIG. 4, the patient recruitment server 16 is provided to dispatch a recruitment notification 76 to a healthcare staff 78 of the hospitals 12. The user interface routine 60 is provided to record a recruitment activation information 80 from the recruitment center 64. The recruitment activation information 80 activates a recruitment for a new recruitment information or advantageously for a recruitment information 62 stored by the search routines 72 of the patient data processing units 14. The search routines 72 of the patient data processing units 14 search the index database 52, on the basis of the recruitment information 62, for corresponding patient data records 32. The search results 74 of the search are forwarded to a notification routine 82 of the patient recruitment server 16 by the search routine 72. The search result 74 herein comprises an information which describes how to contact the healthcare staff 78.

The search routines 72 of the patient data processing units 14 repeatedly carry out the search on the basis of the recruitment information 62, in the present case in an interval that is determinable by the recruitment center 64. As an alternative, the search routine 72 could search only new and modified patient data records 32.

The notification routine 82 dispatches a recruitment notification 76 regarding the patient data records 32 listed in the search result 74 to healthcare staff 78 of the respective hospital 12, in this case as a push message. The patient recruitment server 16 dispatches a recruitment notification 76 to a receiving device that is individually assigned to a person of the healthcare staff 78, in the present case to a pager and/or a mobile phone. The recruitment notification 76 at least indicates that a patient data record 32 corresponding to a patient under treatment in the hospital 12 has been found by means of the recruitment information 62. The recruitment notification 76 could comprise information deemed expedient by the person skilled in the art, e.g. the pseudonym information 36 and/or a number of found patient data records 32. The notification routine 82 is provided to automatically dispatch recruitment notifications 76 regarding patient data records 32 newly found by means of the recruitment information 62 to the healthcare staff 78. As an alternative to the patient recruitment server 16, the patient data processing unit 14 could comprise the notification routine 82.

The notification routine 82 is further provided to dispatch a recruitment specification information 84 to the patient data processing unit 14. The recruitment specification information 84 contains details on a procedure for which the patient is to be recruited, in particular on risks of the procedure and/or on necessary requirements for participation in the procedure.

As shown in FIG. 5, the patient data processing unit 14 receives the recruitment information 62. The search routine 72 of the patient data processing unit 14 identifies the pseudonym information 36 corresponding to the recruitment information 62. As described regarding FIG. 4, the patient recruitment server 16 dispatches the recruitment notification 76 to the healthcare staff 78. The database 56 identifies the patient data records 32 corresponding to the pseudonym information 36 and makes them available to a user interface routine 86 of the patient data processing unit 14, in this case of the patient data processing server 28.

The pseudonym administration server 26 comprises a depseudonymization routine 88 which is provided to determine at least the patient identification information 38 corresponding to the pseudonym information 36 of the pseudonymized patient data records 32. The depseudonymization routine 88 retrieves the patient identification information 38 corresponding to the pseudonym information 36 from the pseudonym database 40. The depseudonymization routine 88 has an interface which is provided to output the patient identification information 38 to the healthcare staff 78. The interface of the depseudonymization routine 88 is in this case embodied as an http server. The interface is protected against unauthorized access.

The user interface routine 86 of the patient data processing server 28 is provided to output the patient identification information 38 to the healthcare staff 78. Moreover, the user interface routine 86 is provided to output the pseudonymized patient data records 32 to the healthcare staff 78. The user interface routine 86 could also be provided to output the original patient data records 22 to the healthcare staff 78. Furthermore, the user interface routine 86 is provided to output the recruitment specification information 84 to the healthcare staff 78. This information allows the healthcare staff to verify the recruitment and to carry out a recruitment interview.

The user interface routine 86 is implemented as an http server. However, as an alternative, any other server types are conceivable. The healthcare staff 78 accesses a website supplied by the user interface routine 86. The website comprises a function for authentification of the healthcare staff 78. From a computer of the healthcare staff 78, the website retrieves the patient identification information 38 from the depseudonymization routine 88 of the pseudonym administration server 26.

The healthcare staff 78 carries out the recruitment interview with the patient. The details thereto required are gathered by the healthcare staff 78 from the recruitment specification information 84. The healthcare staff 78 also carries out, if the patient agrees and if applicable, further examination of the patient, according to the information gathered from the recruitment specification information 84. The healthcare staff 78 ascertains if the patient agrees to the recruitment, if he is suitable for the recruitment or unsuitable for the recruitment.

The user interface routine 86 of the patient data processing server 28 collects a patient status information 90 from the healthcare staff 78, which at least specifies if the patient agrees to the recruitment, is suitable for the recruitment or unsuitable for the recruitment. The patient status information 90 also comprises information on the further examinations of the patient. The patient data processing units 14 send the patient status information 90 to the patient recruitment server 16. The user interface routine 60 of the patient recruitment server 16 outputs the patient status information 90 to the recruitment center 64.

The patient recruitment server 16 has an administration interface 92. An administrator 94 can configure access possibilities of the plurality of recruitment centers 64 and of the healthcare staff 78 by way of the administration interface 92. Furthermore, the administrator 94 can modify other configurations of the patient recruitment system 10, which are deemed expedient by the person skilled in the art. The administration interface 92 may be embodied at least partially together with the user interface routine 60.

The invention claimed is:

1. A patient recruitment system comprising:
   A) at least one patient recruitment server,
      a) being arranged outside intranets of healthcare information systems of healthcare institutions with the healthcare information systems comprising patient data or patient-related data;
      b) comprising at least one search routine configured to dispatch at least a recruitment information comprising recruitment characteristics and to generate search results;
      c) comprising at least one user interface routine which is configured to output the search results of the search routine of the patient recruitment server to a recruitment center;
   B) more than one patient data processors, each of which
      d) being arranged in an intranet of an IT department of a different healthcare institution and located in a place different from the location of the patient recruitment server;
      e) being only connected via the Internet with the patient recruitment server;
      f) only communicating in an encoded manner with the patient recruitment server;
      g) being configured to receive and process patient data records from the healthcare information system of the healthcare institution where the respective patient data processor is located;
      h) being configured to process the patient data records inside the intranet of the healthcare institution where the respective patient data processor is located;
      i) comprising a pseudonymization routine, being configured to
         pseudonymize the patient data records received from the healthcare information system of the healthcare institution where the respective patient data processor is located at, and
         thereby create the pseudonymized patient data records;
      j) comprising at least one patient data processing server, which comprises
         one or more databases exclusively for storing pseudonymized patient data records,
      k) comprising at least one pseudonym administration server, being configured to
         store a pseudonym information, which bijectively identifies a patient data record without allowing conclusions to a patient's identity,
         store the corresponding patient identification information, and
         dispatch the pseudonymized patient data records within the patient data processor to be received by the at least one patient data processing server of the respective patient data processor, and
      l) comprising an individual search routine, being configured to
         receive the recruitment information comprising the recruitment characteristics from the search routine of the patient recruitment server, and
         search the databases of the patient data processing server of the respective healthcare institution on the basis of the recruitment information received from the patient recruitment server,
      wherein the patient data records that are searched by the individual search routines of the patient data processors are implemented as the pseudonymized patient data records, which are stored in the different databases of the patient data processing servers of each of the respective patient data processors of the different healthcare institutions,
      wherein each of the individual search routines of the patient data processors are configured to generate search results for each of the healthcare institutions individually,
      wherein each of the individual search routines of the patient data processors are configured to dispatch the search results to the patient recruitment server, and
      wherein the output search results comprise at least a number of found patient data records but comprise no information suitable for directly identifying a patient whom one of the found patient data records is allocated to.

2. The patient recruitment system according to claim 1, wherein the plurality of patient data processors have at least one respective user interface routine provided to at least partially output at least one of the patient data records to the healthcare staff.

3. The patient recruitment system according to claim 1, wherein the plurality of patient data processors are provided to collect at least one patient status information from the healthcare staff.

4. The patient recruitment system according to claim 1, wherein each of the plurality of patient data processors comprises at least one respective ontology routine provided to standardize at least one ontology of the patient data records.

5. The patient recruitment system according to claim 1, wherein the user interface routine of the patient recruitment server is provided to collect a recruitment information from the recruitment center.

6. The patient recruitment system according to claim 1, wherein the user interface routine of the patient recruitment server is provided to output a number of found patient data records which originate from one of the healthcare information systems.

7. The patient recruitment system according to claim 1, wherein the patient data records comprise biomedical data, medical product data, laboratory data, personal data or sensor data.

8. The patient recruitment system according to claim 1, wherein the pseudonymization routine comprises self-learning functions provided to remove information from patient data records, which could identify the patients from free text contained within the patient data records.

9. A patient recruitment method, with
   at least one patient recruitment server, which is arranged outside intranets of healthcare information systems of healthcare institutions, with the healthcare information systems comprising patient data records or patient-related data;
   and more than one patient data processor, each of which is
      arranged in an intranet of an IT department of a different healthcare institution,
      located in a place different from the location of the patient recruitment server,
      only connected via the Internet with the patient recruitment server,
      only communicating in an encoded manner with the patient recruitment server, and
      comprising at least one patient data processing server with at least one database for storing pseudonymized patient data records, the patient recruitment method comprising the steps of:
- each of the patient data processors receiving and processing the patient data records from the healthcare information system of the healthcare institution where the respective patient data processor is located, wherein each of the patient data processors processes the patient data records only inside the intranet of the healthcare institution where the respective patient data processor is located;
- pseudonymization routines of the respective patient data processors pseudonymizing the patient data records received from the healthcare information system of the healthcare institution where the respective patient data processor is located at, and thereby creating the pseudonymized patient data records,
- pseudonym administration servers of the respective patient data processors storing a pseudonym information, which bijectively identifies a patient data record without allowing conclusions to a patient's identity, storing the corresponding patient identification information, and dispatching the pseudonymized patient data records within the patient data processor to be received by the at least one patient data processing server of the respective patient data processor,
- the at least one database of the respective patient data processing server storing the received pseudonymized patient data records,
- at least one search routine of the at least one patient recruitment server dispatching at least a recruitment information comprising recruitment characteristics to individual search routines of several patient data processors of the patient recruitment system,
- the individual search routines of the patient data processors searching the databases for storing pseudonymized patient data records of the patient data processing servers of each of the respective patient data processors from different healthcare institutions on the basis of the recruitment information received from the patient recruitment server, wherein the patient data records that are searched by the individual search routines of the patient data processors are implemented as the pseudonymized patient data records, which are stored in the databases for storing pseudonymized patient data records of the patient data processing servers of each of the respective patient data processors of the different healthcare institutions,
- the individual search routines of the patient data processors generating generates search results for each of the healthcare institutions individually, and
- the individual search routines of the patient data processors dispatching the search results to the patient recruitment server, wherein the dispatched search results comprise at least a number of found patient data records but comprise no information suitable for directly identifying a patient whom one of the found patient data records is allocated to
- at least one user interface routine of the patient recruitment server outputting the received search results of the individual search routines of the patient recruitment server to a recruitment center.

\* \* \* \* \*